United States Patent [19]

Hildebrand

[11] 4,210,028

[45] Jul. 1, 1980

[54] METHOD AND APPARATUS FOR ULTRASONICALLY MEASURING CONCENTRATIONS OF STRESS

[75] Inventor: B. Percy Hildebrand, Richland, Wash.

[73] Assignee: Electric Power Research Institute, Inc., Palo Alto, Calif.

[21] Appl. No.: 910,788

[22] Filed: May 30, 1978

[51] Int. Cl.² .......................................... G01N 29/04
[52] U.S. Cl. ...................................... 73/598; 73/626
[58] Field of Search .................. 73/597, 598, 602, 626

[56] References Cited

U.S. PATENT DOCUMENTS

| | | | |
|---|---|---|---|
| 3,942,358 | 3/1976 | Pies | 73/626 |
| 4,073,007 | 2/1978 | Boivin | 73/597 |
| 4,096,755 | 1/1978 | Hause et al. | 73/598 |

OTHER PUBLICATIONS

"Stress-Induced Anisotropy in Solids—The Acousto-elastic Effect", by R. T. Smith, *Ultrasonics* Jul.-Sep. 1963, pp. 135-147.
"A Review of the Techniques Using Ultrasonic Waves for the Measurement of Stress Within Materials" by B. J. Ratcliffe, *British Journal of N.D.T.* Sep. 1969, pp. 48-58.
"Second-Order Elastic Deformation of Solids" by D. S. Hughes, *Physical Review*, vol. 92, No. 5, Dec. 1953, pp. 1145-1149.
"Ultrasonic Wave Velocities in Stressed Nickel Steel", *Nature*, Sep. 22, 1962, pp. 1193 & 1194.
"Ultrasonic Measurement of Stresses" by D. I. Crecraft, *Ultrasonics for Industry*, 1967 (conference paper).
"Acoustical Birefringence and the Use of Ultrasonic Waves for Experimental Stress Analysis" by Nelson N. Hsu, *Experimental Mechanics*, May 1974, pp. 169-176.
"Ultrasonic Nondestructive Measurements of Residual Stress" by O. I. Gushcha, et al., Translated from Problemy Prochnosti, No. 8, pp. 71-73, Aug., 1973; original article submitted Jul. 1, 1972; Published by Plenum Publishing Corp., 227 West 17th St. New York, N. Y. 10011.
"An Ultrasonic Technique for the Measurement of Residual Stress" by P. J. Noronka et al., *Journal of Testing and Evaluation*, Mar. 1975, pp. 147-152.
"A Tutorial on Art (Algebraic Reconstruction Techniques)" by Richard Gordon, *IEEE Transactions on Nuclear Science*, vol. NS-21, Jun. 1974, pp. 78-93.
"Algebraic Reconstruction of Spatial Distributions of Acoustic Absorption Within Tissue from their Two-Dimensional Acoustic Projections" by J. F. Greenleaf et al., *Acoustic Holography*, vol. 5, pp. 591-603.
"Algebraic Reconstruction of Spatial Distributions of Acoustic Velocities in Tissue from their Time-Of-Flight Profiles" by J. F. Greenleaf et al., *Acoustic Holography*, vol. 6, pp. 71-90.
"Refractive Index By Reconstruction: Use to Improve Compound B-Scan Resolution" by J. F. Greenleaf et al., *Acoustic Holography*, vol. 7, pp. 263-273.
"Reconstructing Three-Dimensional Fluid Velocity Vector Fields from Acoustic Transmission Measurements" by S. A. Johnson et al., *Acoustic Holography*, vol. 7, pp. 307-326.

*Primary Examiner*—Anthony V. Ciarlante
*Attorney, Agent, or Firm*—Flehr, Hohbach, Test, Albritton & Herbert

[57] ABSTRACT

An apparatus for ultrasonically measuring concentrations of stress in objects of interest. The apparatus includes an ultrasonic transducer array for propagating acoustic waves in an object of interest along a plurality of determinable directions and from a plurality of determinable positions. A time interval counter measures the time of flight of the acoustic waves along the determinable directions and from the determinable positions. The time of flight measurements are reconstructed into a map of the variations in acoustic velocity within the object. The changes in acoustic velocity are then mathematically converted into a map of stress concentration areas in the object of interest.

10 Claims, 9 Drawing Figures

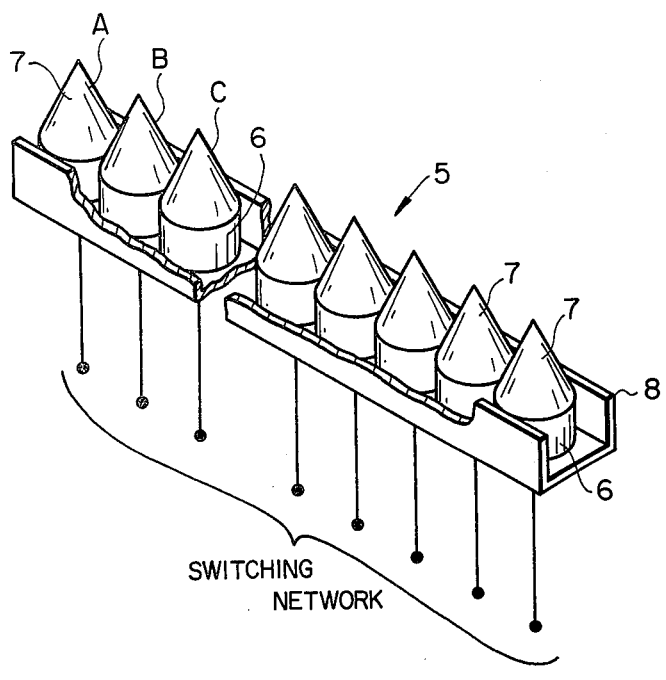
FIG_1
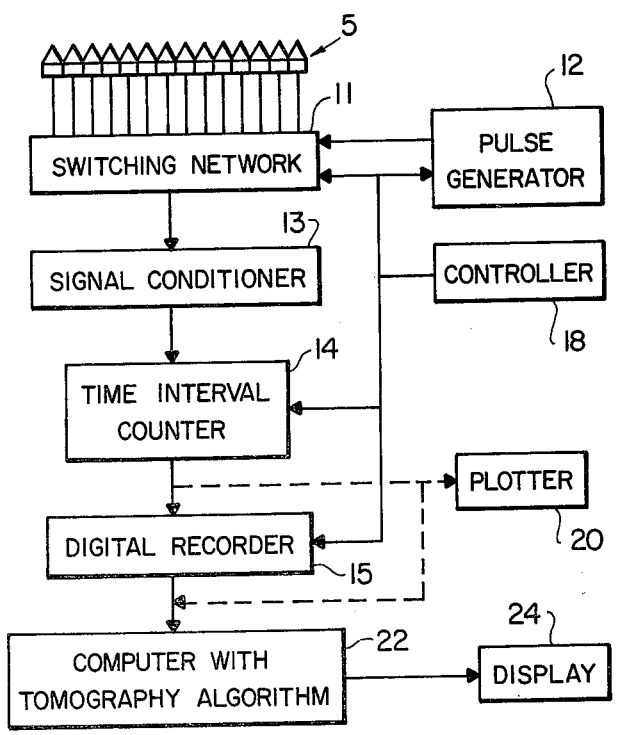
FIG_2
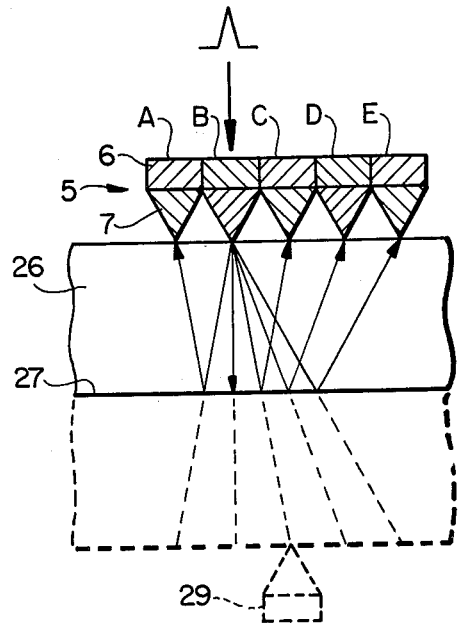
FIG_3
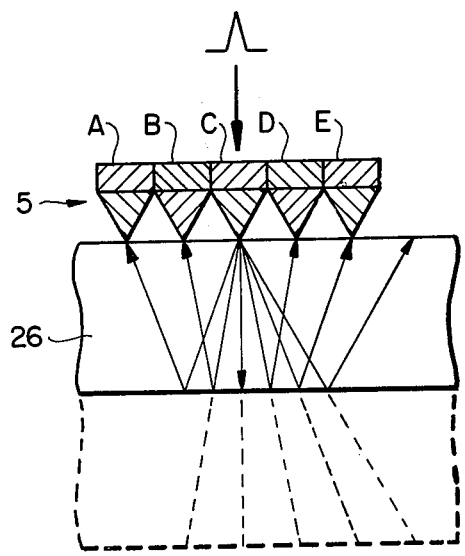
FIG_4

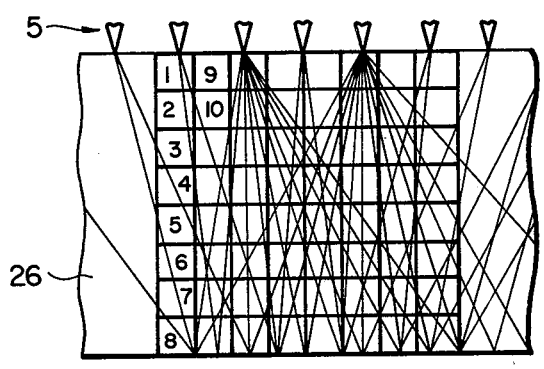
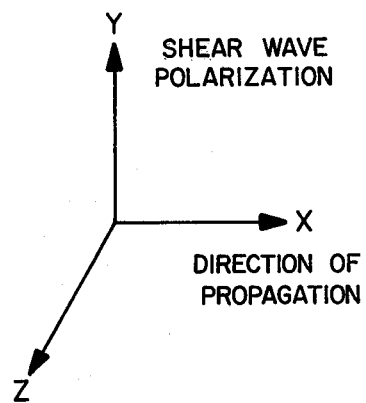
FIG__5         FIG__6
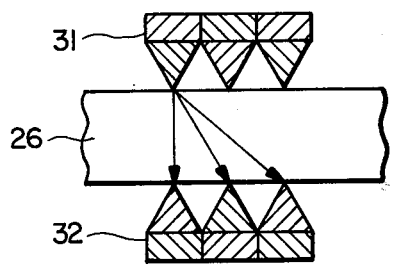
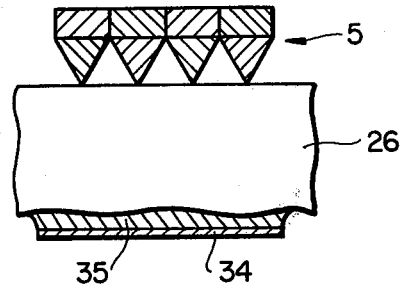
FIG__7         FIG__8
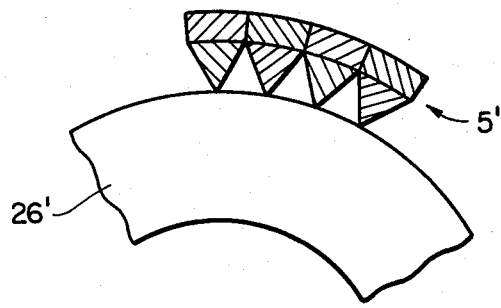
FIG__9

METHOD AND APPARATUS FOR ULTRASONICALLY MEASURING CONCENTRATIONS OF STRESS

BACKGROUND OF THE INVENTION

This invention generally relates to systems for measuring areas of residual stress in structures and, more particularly to ultrasonic systems for making such measurements.

In the manufacture of large structures such as pressure vessels a number of large welds are required. After welding the heat affected zones surrounding these welds usually contain residual stress due to uneven cooling rates. One procedure that is widely performed to relieve these residual stresses is so heat the entire structure to an appropriate temperature and thereafter to carefully control its rate of cooling.

At the present time there is no satisfactory test for actually measuring the success of this stress relief procedure. Now and then high residual stress regions exist in the structure after completion of the procedure and if these regions occur in critical areas, cracks develop and fracture can occur.

Currently, the standard non-destructive testing procedures consist of radiography and ultrasonic pulse echo. Neither of these techniques, however, can reveal the presence of residual stress. Radiography records only the variations in the specific gravity of the material being tested. Ultrasonic imaging cannot be used to reveal areas of residual stress because these regions are not sharply defined and hence do not reflect sufficient acoustic waves to be measured.

It is well known that the velocity of sound in a solid is affected by the residual stresses. This phenomenon is a third order effect and has been used as a research tool to determine the Lame and Murnaghan elastic constants for various materials. It is also known that the elastic constants are related to the velocity of sound in solid materials.

OBJECTS AND SUMMARY OF THE INVENTION

It is an object of the present invention to locate and measure areas of residual stress in structures. This object is achieved by an ultrasonic array for transmitting acoustic waves along a plurality of determinable directions and from a plurality of determinable positions in an object of interest. The times of flight of the acoustic waves travelling along these directions and from these positions are measured and a map of the changes in acoustic velocity is reconstructed using computed axial tomography. The changes in acoustical velocity are thereafter mathematically converted into a stress concentration map of the object of interest.

Another object of the present invention is to propagate acoustic waves in an object of interest along determinable directions and from determinable positions. This object is achieved by a transducer array having a plurality of transducer elements each with a tapered coupling element for point contact with an object of interest.

The foregoing and other objects are achieved by a method and apparatus for ultrasonically measuring stress concentrations in objects of interest. The apparatus includes an ultrasonic transducer array for propagating acoustic waves along a plurality of determinable directions and from a plurality of determinable positions in the object of interest. A time interval counter measures the time of flight of the acoustic waves along the paths and from each of the positions within the object of interest. The time of flight measurements are reconstructed using computed axial tomography into a crossectional map of the variations in the acoustic velocity in the object. The variations in acoustic velocity are thereafter mathematically converted into a map of stress concentration in the object of interest.

BRIEF DESCRIPTION OF THE DRAWINGS

FIG. 1 is an isometric view, partially cut away and partially broken away, of an ultrasonic transducer array according to the present invention.

FIG. 2 is a block diagram of an apparatus for measuring stress concentrations in an object of interest according to the present invention.

FIGS. 3 and 4 illustrate the propagation of acoustic waves by the transducer array of FIG. 1 in a reflection mode.

FIG. 5 is a diagrammatic view of the object of interest illustrating how it is divided into small cells for reconstructing a map of the variations in acoustic velocity from the time of flight measurements.

FIG. 6 is an illustration of the coordinate system used in connection with the equations for converting the variations in acoustic velocity into a map of the areas of stress concentration.

FIG. 7 is a diagrammatic view of the array of FIG. 1 illustrating its operation in a transmission mode.

FIG. 8 is a diagrammatic view of the transducer array of FIG. 1 illustrating the use of a reflective plate located beyond the object of interest.

FIG. 9 is a diagrammatic view of the transducer array of FIG. 1 illustrating its operation on an object of interest having a curved surface.

DESCRIPTION OF THE PREFERRED EMBODIMENTS

DESCRIPTION OF THE APPARATUS

Referring to FIG. 1, reference numeral 5 indicates an ultrasonic transducer array according to the present invention. The array includes a plurality of ultrasonic transducer elements 6 that are fabricated from conventional materials and are mounted in a row. The array includes between twenty to thirty elements and each element has the shape of a right circular cylinder. The elements are nominally one half inch in diameter and are each bonded to a tapered acoustic wave coupling element 7. The coupling elements have the shape of a right circular cone and are fabricated from a metal of sufficient hardness to permit the array to be pressure coupled to an object of interest via the sharp points. The transducer elements and the coupling elements are maintained in alignment by a U-shaped channel 8. The channel maintains the spacing between the tips of the coupling elements so that acoustic waves can be propagated from the array into an object of interest along a plurality of determinable directions and from a plurality of determinable positions. The array introduces spherically spreading acoustic waves into the object of interest at the point of contact of each coupling element.

Referring to FIG. 2, the transducer array 5 is energized by a pulse generator 12 through a switching network 11. The switching network is of known construction and connects the pulse generator to each transducer element in turn under the command of the controller 18. The pulse generator has an output of high voltage pulses and operates at a frequency sufficiently high to insure that the rise time of the acoustic waves is steep enough to obtain an accurate measurement of the time of flight. The switching network 11 also connects the transducer elements one by one to a signal conditioner 13 and to a time interval counter 14 when the apparatus is operating as a receiver. The purpose of the signal conditioner is to amplify the signal and set a threshold to which the time interval counter is triggered.

In one embodiment actually constructed, a Metrotek MP 215 high energy pulser driving a wide band transducer was used for the pulse generator 12. A Metrotek MR 101 receiver amplifier and a Metrotek MG-703 time interval gate was used for the signal conditioner 13. The Metrotek equipment is available from Metrotek, Inc. of Richland, Wash. A Hewlett-Packard HP 5345A time interval counter was used to measure the times of flight and to convert the measurements into digital data. The operating frequency was 2MHz.

The apparatus is sequenced by a controller 18, FIG. 2. The controller orders the switching network 11 to select the desired transmitting and receiving transducers and triggers the pulse generator 12. The controller also triggers the time interval counter 14 and alerts the digital recorder 15. In the preferred embodiment a Hewlett-Packard HP 9825A programmable calculator was used for the controller.

The time interval counter 14, FIG. 2 has a digital output which is recorded by a digital recorder 15. The digital data is recorded on magnetic tape in a cassette. The cassette permits subsequent processing of the measurements at a location remote from the object of interest. A plotter 20 for evaluating raw data is also connected to the time interval counter. In the preferred embodiment a Hewlett-Packard HP 9862A plotter was used and was controlled by the Hewlett-Packard programmable calculator identified above. The digital time of flight measurements and the corresponding directional and positional data are transmitted to a digital computer 22 which executes a computed axial tomography (CAT) program. A brief description of this program is given below in section III. The output of the computer is connected to a visual display device 24 which presents a map of the areas of stress concentration in the object of interest. In the preferred embodiment a Digital Equipment Corporation PDP-11/70 computer was used to reconstruct the variations in acoustic velocity and to calculate the areas of stress concentration.

OPERATION OF THE APPARATUS

To take a set of measurements, each transducer element 6, FIG. 1 in the array is individually energized one after the other. During the interval that each transducer is selected to be pulsed, the other transducers in the array act as receivers. The time of flight of the acoustic waves along each ray path from each transducer to the other transducers are measured by the time interval counter.

FIGS. 3 and 4 illustrate the pulsing and receiving modes of the array. In FIG. 3 transducer element B is pulsed and the acoustic waves radiate therefrom in a spherically spreading pattern in the object of interest 26. The waves are reflected by the opposite surface 27 of the object of interest 26 and are detected by each of the transducer elements in the array in turn. In FIG. 4 transducer element C is pulsed.

The reflection mode of operation illustrated in FIGS. 3 and 4 is used when only a single surface of the object of interest is available for inspection. When both sides of the object are available, then two arrays are used in a transmission mode as illustrated in FIG. 7.

It should be noted in FIG. 3 that when acoustic waves are reflected by the opposite surface 27 of the object of interest, any reconstruction of the data includes a mirror image of the object as well as the image of the object itself. The mirror image is illustrated in FIGS. 3 and 4 in phantom lines and the image of the receiver is indicated by reference numeral 29.

The operator of the apparatus initially carries the instrument to the inspection site and brings the transducer array 5, FIG. 1 into direct physical contact with the structure being scanned. The array 5, switching network 11, pulse generator 12, controller 18, signal conditioner 13, time interval counter 14 and digital recorder 15 are all portable. The operator takes one set of data as described below, then rotates the transducer array and repeats the process. For a complete three dimensional inspection of the object of interest, the transducer array 5 is rotated in steps through 180°. Alternatively, the operator translates the array in a parallel direction to obtain data corresponding to a set of parallel slices through the region of interest. The data recorded at the inspection site is then transmitted to a central computer 22 for reconstruction. This transmission of data can be done either over a telephone line or by the transport of the tape cassette.

At the inspection site, the transducer array is actuated in accordance with the following steps:

1. The first transducer A, FIG. 1 in the array 5 is selected by the switching network 11, FIG. 2 and is pulsed by the pulse generator 12. The transducer is driven with a single high voltage pulse that generates a steep front pressure wave that propagates into the object of interest. The transducer generates acoustic waves that propagate into the object of interest as spherical waves diverging from the point of contact of the tip of the coupling element 7. The pulse generator, the time interval counter, and the digital recorder 15 are triggered by the controller 18.

2. Immediately after transmission all the transducers in the array including the first transducer are switched into the receive mode.

3. The first reflector pulse detected by the transducer array is passed by the switching network 11 through the signal conditioner 13 and is used to turn off the time interval counter 14. Thereafter the time interval counter computes the time of flight, digitizes the measurement and passes the data to the digital recorder 15 where the measurement is stored. Data from the controller 18 fully identifying the transducer is also stored so that the time of flight can be later identified and the path computed.

4. Steps 1 and 2 are repeated with the switching network 11 selected to pass the reflected pulse to the time interval counter 14 for transducers lattered B onward. In other words, the first transducer A is pulsed again and again and the reflected wave is first detected by the first transducer A, then by the second transducer B and by the third C. etc. in turn. Each time of flight is recorded by the digital recorder 15 along with data identifying the source and receiver transducers.

5. The switching network 11 is then selected by the controller 18 so that the pulse generator drives the second transducer B in the array. Steps 2 through 4 are repeated.

6. Step 5 is repeated for all of the transducers in the array.

In summary, the switching network 11 connects up every transducer in the array so that the time of flight between every pair of transducers is measured and recorded.

The time of flight measurements derived from the reflection of acoustic waves received by the same transducer that was used as the transmitter are used to provide information about the geometry of the material. If, for example, a section of the object of interest has a wedge or curved shape, this may affect the reconstruction. The computer program uses this information to find a path length that each ray should have if the acoustic velocity were constant in the object of interest. This data is factored into the reconstruction process to obtain a geometrically correct image.

As discussed below, an independent measurement of the thickness of the specimen is made concurrently with the time of flight measurements. Thickness can be measured by either a differential capacitive sensor, a differential LVDT system or by direct micrometer measurements.

COMPUTER RECONSTRUCTION OF DATA

The time of flight measurements made by the array 5, FIG. 1 and recorded by the digital recorder 15, FIG. 2 are converted into quantitative maps of velocity variation within the object of interest. The time of flight profiles through each section of the object of interest are made from many angular directions. A digital computer processes the profiles and reconstructs a cross-sectional velocity distribution to match the measured data.

The technique of cross-sectional mapping from a multiplicity of profiles was first studied by Radon in 1917. This mathematical technique later was caled computed axial tomography (CAT) and is used in commercial x-ray scanners. The present invention operates in a similar manner using a PDP-11/70 digital computer manufactured by the Digital Equipment Corporation. This computer operates with a tomography algorithm and currently uses the ART program available from the open technical literature.

To perform tomography algorithm, the computer mathematically divides the object of interest 26, FIG. 5 into a plurality of cells. Knowing the direction of propagation of each acoustic wave and its precise point of origin, the computer calculates the path length, $L_{ij}$ of each wave i through each cell j. Each cell is assigned a value of acoustic velocity $V_j$. The pertinent set of equations to be solved by the computer are:

$$\{T_i\} = \sum_j \frac{L_{ij}}{V_j} + \frac{1}{V_\omega}\left(L - \sum_j L_{ij}\right)$$

where $T_i$ = total time of flight along $i^{th}$ ray
$V_j$ = velocity in $j^{th}$ cell
$V_\omega$ = velocity in coupling medium
$L$ = total geometric path length
$L_{ij}$ = path length of the $i^{th}$ ray in the $j^{th}$ cell If a sufficient number of time of flight profiles are taken by the array, there are as many knowns $T_i$ as unknowns $V_j$ and the set of simultaneous equations can be solved for the $V_j$.

Although the program identified above is used in the preferred embodiment there are many algorithms that may be used to solve this set of equations. The most direct method is matrix inversion but it is also the most time consuming since no attempt is made to simply the matrix. Other algorithms use the techniques of arithmatic reconstruction by interation, convolution and Fourier transform.

CONVERSION OF DATA TO A STRESS CONCENTRATION MAP

In section III the calculation of a map of the variations in acoustic velocity within the object of interest is described. The reconstructed changes in velocity are converted into expressions equivalent to residual stress by the equations listed below.

Acoustelasticity is analagous to photoelasticity in that the wave velocities are stress dependent. However, since sound waves can be both longitudinal or transverse, the phenomenon and mathematical description of acoustoelasticity is more complex. The following seven equations define stress dependence of ultrasonic velocities in a material which is initially isotropic. These equations correspond to the coordinate system illustrated in FIG. 6.

$$\rho_o V_{lp}^2 = \lambda + 2\mu - \frac{P}{3K_o}(7\lambda + 10\mu + 6l + 4m) \quad 2.$$

$$\rho_o V_{sp}^2 = \mu - \frac{P}{3K_o}\left(3\lambda + 6\mu + 3m - \frac{n}{2}\right) \quad 3.$$

$$\rho_o V_{lx}^2 = \lambda + 2\mu + \frac{T}{3K_o}\left[\frac{\lambda + \mu}{\mu}(4\lambda + 10\mu + 4m) + \lambda + 2l\right] \quad 4.$$

$$\rho_o V_{lx}^2 = \lambda + 2\mu - \frac{T}{3K_o}\left[\frac{2\lambda}{\mu}(\lambda + 2\mu + m) - 2l\right] \quad 5.$$

$$\rho_o V_{sx}^2 = \mu + \frac{T}{3K_o}\left(4\lambda + 4\mu + m + \frac{\lambda n}{4\mu}\right) \quad 6.$$

$$\rho_o V_{sy}^2 = \mu + \frac{T}{3K_o}\left(\lambda + 2\mu + m + \frac{\lambda n}{4\mu}\right) \quad 7.$$

$$\rho_o V_{sz}^2 = \mu - \frac{T}{3K_o}\left(2\lambda - m + \frac{n}{2} + \frac{\lambda n}{2\mu}\right) \quad 8.$$

Where $\rho_o$ = density of unstrained material
$V$ = ultrasonic velocity
$\lambda, \mu$ = second order Lamé elastic constants
$l, m, n$ = third order Murnaghan elastic constants
$P$ = hydrostatic pressure
$T$ = unaxial tension
$K_o = \frac{1}{3}(3\lambda + 2\mu)$ = bulk modulus
1st subscript $l$ refers to longitudinal wave
1st subscript $s$ refers to shear wave
2nd subscript $p$ refers to hydrostatic pressure
2nd subscript $x$, $y$ or $z$ refers to uniaxial tension, in the $x$, $y$ or $z$ direction respectively The above equations permit the map of velocity changes to be converted to a map labled in terms of stress.

Applications

The preferred embodiment can be used, inter alia, for mapping stress anomalies in large pressure vessels. These vessels have metal sections that are between four and ten inches in thickness and contain numerous large welds. The maps of the residual stress around the welded areas of the vessels are used for fracture analysis and post-welding stress relief.

In one application of the preferred embodiment velocity anomalies as low as 0.2% were mapped and it is believed that 0.05% is feasable. This order of sensitivity allows stress anomalies as low as 1,000 psi/inch in steel to be mapped.

FIG. 7 illustrates an alternative embodiment of the present invention which can be used when both surfaces of the object of interest 26 are accessible. Two subarrays are used; one subarray 31 acts as the source array and the other subarray 32 as the receiver array. The use of two subarrays has application for very thick materials and materials that tend to attenuate acoustic wave propagation. The embodiment of FIG. 7 also has the advantage of limiting the length of the array necessary to obtain sufficient measurements. That is to say, if the reflection mode, FIG. 3 is used than a single array must be used that is as long as the two arrays 31, 32, FIG. 7 combined. In both cases the arrays gather data over a ±45° field of view. The method of operation and reconstruction of two arrays is similar to the procedure described above in sections II to IV.

It is contemplated that there are objects of interest having a bottom surface which is not sufficiently smooth to act as a good reflector when the apparatus is operated in the reflection mode as illustrated in FIG. 3. In this case a smooth reflector 34, FIG. 8 is introduced behind the surface and is coupled to the object of interest by a velocity matching medium 35. If the acoustic velocity in the couplant is not precisely equal to that in the object of interest, the region between the reflector 34 and the object of interest will appear as a velocity anomaly in the reconstruction. This anomaly will be of known magnitude and position and thus can be disregarded.

In the preferred embodiment described above, the transducers 6, FIG. 1 are coupled to the object of interest 26 by a plurality of cone-shaped coupling elements 7. The present invention also contemplates that other coupling means can be used. For example, the transducer elements can be bonded to an acoustic lens which focuses the acoustic waves through a water stand-off coupling chamber and onto the surface of the object of interest. Thus, any means for introducing spherically spreading waves into the object of interest from a definable point and along a definable direction of propagation can be used.

The present invention can also be employed on curved surfaces such as piping and cylindrical pressure vessels. Referring to FIG. 9, the apparatus for holding the transducers (not shown) is sufficiently flexible so that it conforms to a curved surface 26'. In the calculation of velocity variation the computer compensates for the curved shape by using the data obtained from the source transducer as described in section II.

Although the apparatus illustrated in FIG. 2 only measures time of flight, the attenuation of the acoustic waves along each path can also be measured. An amplitude measuring system such as a digital volt meter can be attached to the output of the signal conditioner 13, FIG. 2 so that attenuation can be recorded by the apparatus as well as the time of flight. These measurements, when provided to the computer 22, permit the reconstruction of images of both acoustic velocity and acoustic attenuation.

Thus, although the best modes contemplated for carrying out the present invention have been herein shown and described, it will be apparant that modification and variation may be made without departing from what is regarded as the subject matter of the invention.

What is claimed is:

1. An apparatus for ultrasonically measuring stress concentrations in an object of interest, comprising:
   (a) an ultrasonic transducer array of propagating acoustic waves in an object of interest along a plurality of determinable directions and from a plurality of determinable positions;
   (b) means for placing said transducer array in a plurality of different locations on said object of interest to provide a different plurality of determinable positions;
   (c) means for measuring the time of flight of the acoustic waves within the object of interest along the determinable directions and from the determinable positions; and
   (d) means for storing said time of flight measurements for subsequent processing into a three-dimensional map of stress concentrations in the object of interest.

2. The apparatus of claim 1 wherein the storing means is a digital recorder and the time of flight measurements are storeable on magnetic tape for subsequent processing at a location remote from the object of interest.

3. The apparatus of claim 1 wherein the transducer array both generates and detects acoustic waves in the object of interest, said acoustic waves being reflected within the object of interest by a surface thereof located opposite the array.

4. The apparatus of claim 1 wherein the array includes a first sub-array of elements for transmitting acoustic waves into the object of interest and a second sub-array of elements located opposite said first sub-array for detecting acoustic waves transmitted through the object of interest.

5. The apparatus of claim 1 including
   means for determining from said time of flight measurements any variations in the acoustic velocity of the acoustic waves within the object of interest and for converting said variations in velocity into said three dimensional map of stress concentrations in the object of interest.

6. The apparatus of claim 1 wherein the transducer array includes:
   (a) a plurality of ultrasonic transducer elements;
   (b) a plurality of tapered, acoustic wave coupling elements, each coupling element being attached to a corresponding transducer element for acoustic wave propagation; and
   (c) means for aligning the tapered coupling elements on an object of interest with a predetermined spacing so that the positions and the directions at which acoustic waves are propagated in the object of interest are precisely definable.

7. The apparatus of claim 1 wherein the transducer array includes:
   (a) a plurality of ultrasonic transducer elements;
   (b) a plurality of lenses for focusing acoustic waves, each transducer element being attached to a lens; and
   (c) means for positioning the transducer elements and the lenses with respect to the object of interest so that spherically spreading acoustic waves having determinable directions of propagation and determinable points of origin are introduced into the object of interest.

8. The apparatus of claim 1 including means for sequentially activating each of said transducer elements one at a time, to generate acoustic waves in said object of interest whereby said plurality of determinable positions is provided.

9. An apparatus for ultrasonically measuring stress concentrations in an object of interest, comprising:
  (a) an ultrasonic transducer array for propagating acoustic waves in an object of interest along a plurality of determinable directions and from a plurality of determinable positions;
  (b) means for measuring the time of flight of the acoustic waves within the object of interest along the determinable directions and from the determinable positions; and
  (c) means for determining from said time of flight measurements any variations in the acoustic velocity of the acoustic waves within the object of interest and for converting said variations in velocity into a map of stress concentrations in the object of interest, said means for determining dividing the object of interest into a plurality of cells and solving the following set of equations for $V_j$, the acoustic velocity within each cell:

$$\{T_i\} = \sum_j \frac{L_{ij}}{V_j} + \frac{1}{V_\omega}\left(L - \sum_j L_{ij}\right)$$

where $T_i$ = total time of flight along $i^{th}$ ray
$V_j$ = velocity in $j^{th}$ cell
$V_\omega$ = velocity in coupling medium
$L$ = total geometric path length
$L_{ij}$ = path length of the $i^{th}$ ray in the $j^{th}$ cell 10. An apparatus for ultrasonically measuring stress concentrations in an object of interest, comprising:
  (a) an ultrasonic transducer array for propagating acoustic waves in an object of interest along a plurality of determinable directions and from a plurality of determinable positions;
  (b) means for measuring the time of flight of the acoustic waves within the object of interest along the determinable directions and from the determinable positions; and
  (c) means for determining from said time of flight measurements any variations in the acoustic velocity of the acoustic waves within the object of interest and for converting said variations in velocity into a map of stress concentrations in the object of interest, said means for converting the variations in velocity into a map of stress concentrations solving the following equations:

$$\rho_0 V_{lp}^2 = \lambda + 2\mu - \frac{P}{3K_o}(7\lambda + 10\mu + 6l + 4m) \quad 2.$$

$$\rho_0 V_{sp}^2 = \mu - \frac{P}{3K_o}\left(3\lambda + 6\mu + 3m - \frac{n}{2}\right) \quad 3.$$

$$\rho_0 V_{lx}^2 = \lambda + 2\mu + \quad 4.$$
$$\frac{T}{3K_o}\left[\frac{\lambda+\mu}{\mu}(4\lambda + 10\mu + 4m) + \lambda + 2l\right]$$

$$\rho_0 V_{lx}^2 = \lambda + 2\mu - \frac{T}{3K_o}\left[\frac{2\lambda}{\mu}(\lambda + 2\mu + m) - 2l\right] \quad 5.$$

$$\rho_0 V_{sx}^2 = \mu + \frac{T}{3K_o}\left(4\lambda + 4\mu + m + \frac{\lambda n}{4\mu}\right) \quad 6.$$

$$\rho_0 V_{sy}^2 = \mu + \frac{T}{3K_o}\left(\lambda + 2\mu + m + \frac{\lambda n}{4\mu}\right) \quad 7.$$

$$\rho_0 V_{sz}^2 = \mu - \frac{T}{3K_o}\left(2\lambda - m + \frac{n}{2} + \frac{\lambda n}{2\mu}\right) \quad 8.$$

Where $\rho_0$ = density of unstrained material
$V$ = ultrasonic velocity
$\lambda, \mu$ = second order Lamé elastic constants
$l, m, n,$ = third order Murnaghan elastic constants
$P$ = hydrostatic pressure
$T$ = unaxial tension
$K_o = \frac{1}{3}(3\lambda + 2\mu)$ = bulk modulus
1st subscript $l$ refers to longitudinal wave
1st subscript $s$ refers to shear wave
2nd subscript $p$ refers to hydrostatic pressure
2nd subscript $x, y$ or $z$ refers to uniaxial tension, in the $x, y$ or $z$ direction respectively.

* * * * *